(12) United States Patent
Nigg et al.

(10) Patent No.: US 11,976,832 B2
(45) Date of Patent: May 7, 2024

(54) SYSTEM AND METHOD FOR ASSURING BUILDING AIR QUALITY

(71) Applicant: Integrated Energy Services Corporation, New York, NY (US)

(72) Inventors: Brock L. Nigg, Darien, CT (US); Steve Schlanger, Flagstaff, AZ (US); Frank Ableson, Stanhope, NJ (US)

(73) Assignee: INTEGRATED ENERGY SERVICES CORPORATION, New York, NY (US)

( * ) Notice: Subject to any disclaimer, the term of this patent is extended or adjusted under 35 U.S.C. 154(b) by 0 days.

(21) Appl. No.: 17/006,178

(22) Filed: Aug. 28, 2020

(65) Prior Publication Data

US 2021/0071894 A1 Mar. 11, 2021

Related U.S. Application Data

(60) Provisional application No. 62/898,248, filed on Sep. 10, 2019.

(51) Int. Cl.
*F24F 11/46* (2018.01)
*F24F 11/39* (2018.01)
(Continued)

(52) U.S. Cl.
CPC .............. *F24F 11/46* (2018.01); *F24F 11/39* (2018.01); *F24F 11/47* (2018.01); *F24F 11/52* (2018.01);
(Continued)

(58) Field of Classification Search
CPC .................................................... F24F 11/39
See application file for complete search history.

(56) References Cited

U.S. PATENT DOCUMENTS 4,481,596 A 11/1984 Townzen
4,532,013 A 7/1985 Dietz et al.
(Continued)

FOREIGN PATENT DOCUMENTS

CN 109028510 A 12/2018
EP 3270118 A1 1/2018
RU 2439442 C1 1/2012

OTHER PUBLICATIONS

Hagan et al., "Calibration and Assessment of Electrochemical Air Quality Sensors by Co-Location with Regulatory-Grade Instruments", Atmospheric Measurement Techniques, 2018, pp. 315-328.

(Continued)

*Primary Examiner* — Nathan L Laughlin
(74) *Attorney, Agent, or Firm* — M&B IP Analysts, LLC

(57) ABSTRACT

A system and method for centrally assuring building air quality are provided. The method includes collecting, from a set of sensors of a plurality of sensors, at least air quality data, wherein the plurality of sensors are installed in different locations within a building; analyzing the collected air quality data to determine an air-quality level across different locations within the building; determining whether an adjustment to at least one control device is required, wherein the determination is based on the determined air-quality level and at least one energy-consumption parameter; and actuating at least one building control device when an adjustment is required, wherein actuating at least one building control device allows for control of air quality across different locations within the building.

31 Claims, 9 Drawing Sheets

(51) Int. Cl.
| | |
|---|---|
| *F24F 11/47* | (2018.01) |
| *F24F 11/52* | (2018.01) |
| *F24F 11/58* | (2018.01) |
| *F24F 11/63* | (2018.01) |
| *G01N 33/00* | (2006.01) |
| *G08C 17/02* | (2006.01) |
| *H04W 52/02* | (2009.01) |
| *F24F 110/10* | (2018.01) |
| *F24F 110/20* | (2018.01) |
| *F24F 110/40* | (2018.01) |
| *F24F 110/50* | (2018.01) |
| *F24F 110/66* | (2018.01) |
| *F24F 110/70* | (2018.01) |
| *F24F 110/74* | (2018.01) |
| *F24F 140/60* | (2018.01) |

(52) U.S. Cl.
CPC ............. *F24F 11/58* (2018.01); *F24F 11/63* (2018.01); *G01N 33/0006* (2013.01); *G01N 33/0073* (2013.01); *G01N 33/0075* (2013.01); *G08C 17/02* (2013.01); *H04W 52/0206* (2013.01); *H04W 52/0235* (2013.01); *F24F 2110/10* (2018.01); *F24F 2110/20* (2018.01); *F24F 2110/40* (2018.01); *F24F 2110/50* (2018.01); *F24F 2110/66* (2018.01); *F24F 2110/70* (2018.01); *F24F 2110/74* (2018.01); *F24F 2140/60* (2018.01); *G08C 2201/12* (2013.01); *G08C 2201/40* (2013.01)

(56) References Cited

U.S. PATENT DOCUMENTS

| | | | |
|---|---|---|---|
| 4,858,615 | A | 8/1989 | Meinema |
| 5,016,198 | A | 5/1991 | Schreiber |
| 5,321,638 | A | 6/1994 | Witney |
| 5,498,872 | A | 3/1996 | Stedman et al. |
| 6,581,435 | B2 | 6/2003 | Wang et al. |
| 6,903,330 | B2 | 6/2005 | Evans et al. |
| 6,908,224 | B2 | 6/2005 | Schneider et al. |
| 7,571,065 | B2 | 8/2009 | Seesink |
| 7,599,815 | B2 | 10/2009 | Reichel et al. |
| 8,428,909 | B2 | 4/2013 | Collins |
| 8,682,937 | B2 | 3/2014 | Ludwig |
| 9,213,016 | B1 | 12/2015 | Stetter et al. |
| 9,756,403 | B2 | 9/2017 | Proud |
| 10,349,873 | B2 | 7/2019 | Kamath et al. |
| 10,687,231 | B1 | 6/2020 | Stamatakis |
| 10,712,264 | B2 | 7/2020 | Carbonelli et al. |
| 10,724,976 | B2 | 7/2020 | Rogers et al. |
| 10,757,750 | B2 | 8/2020 | Agiwal et al. |
| 10,758,665 | B2 | 9/2020 | Igarashi et al. |
| 10,827,980 | B2 | 11/2020 | Shariati et al. |
| 11,141,549 | B2 | 10/2021 | Tolmie et al. |
| 11,346,554 | B2 | 5/2022 | Shuk et al. |
| 2003/0080288 | A1 | 5/2003 | Evans et al. |
| 2003/0145644 | A1 | 8/2003 | Rabbett et al. |
| 2007/0242688 | A1 | 10/2007 | McFarland |
| 2009/0012738 | A1 | 1/2009 | Hart et al. |
| 2010/0081411 | A1 | 4/2010 | Montenero |
| 2010/0177750 | A1 | 7/2010 | Essinger et al. |
| 2011/0074552 | A1 | 3/2011 | Norair et al. |
| 2012/0242453 | A1 | 9/2012 | Delgado et al. |
| 2012/0277566 | A1 | 11/2012 | Kamath et al. |
| 2012/0303164 | A1 | 11/2012 | Smith et al. |
| 2013/0038470 | A1 | 2/2013 | Niemeyer et al. |
| 2013/0174646 | A1 | 7/2013 | Martin |
| 2013/0298642 | A1 | 11/2013 | Gillette |
| 2014/0009268 | A1 | 1/2014 | Oshima et al. |
| 2014/0037506 | A1 | 2/2014 | Miki et al. |
| 2014/0053586 | A1 | 2/2014 | Poecher et al. |
| 2014/0126382 | A1 | 5/2014 | Tian et al. |
| 2014/0129004 | A1* | 5/2014 | Takayama ........... H04L 12/2816 700/83 |
| 2014/0247140 | A1 | 9/2014 | Proud |
| 2015/0057960 | A1 | 2/2015 | Dinechin |
| 2015/0096352 | A1 | 4/2015 | Peterson et al. |
| 2015/0195780 | A1 | 7/2015 | Liu |
| 2015/0285755 | A1 | 10/2015 | Moss et al. |
| 2016/0116181 | A1 | 4/2016 | Aultman et al. |
| 2016/0135242 | A1 | 5/2016 | Hampel et al. |
| 2016/0255697 | A1 | 9/2016 | Bhide |
| 2016/0360300 | A1 | 12/2016 | Proud |
| 2018/0120279 | A1 | 5/2018 | Yi et al. |
| 2018/0156484 | A1 | 6/2018 | Kim et al. |
| 2018/0356809 | A1 | 12/2018 | Trainor et al. |
| 2019/0012903 | A1 | 1/2019 | Cai et al. |
| 2020/0003447 | A1* | 1/2020 | Lee .......................... F24F 11/65 |
| 2020/0300756 | A1 | 9/2020 | Carbonelli et al. |
| 2020/0316282 | A1 | 10/2020 | Igarashi |
| 2020/0393152 | A1* | 12/2020 | Ramirez .................. F24F 1/42 |
| 2021/0041125 | A1* | 2/2021 | Liu .......................... F24F 11/65 |
| 2021/0058826 | A1 | 2/2021 | Mao et al. |
| 2022/0003581 | A1 | 1/2022 | Fox et al. |

OTHER PUBLICATIONS

International Search Report and Written Opinion of International Searching Authority for PCT/US2020/048472, ISA/RU, Moscow, Russia, dated Nov. 19, 2020.

International Search Report and Written Opinion of International Searching Authority for PCT/US2020/049934, ISA/RU, Moscow, Russia, dated Nov. 11, 2020.

International Search Report and Written Opinion of International Searching Authority for PCT/US2020/050198, ISA/RU, Moscow, Russia, dated Nov. 13, 2020.

GasAlertMicro 5 02, CO, H2S, PH3, SO2, CI2, NH3, No. 2, HCN, ClO2, 03, VOC, and Combustibles 1, 2, 3, 4, and 5 Gas Detectors User Manual, BW Technologies, Copyright 2005, available online at least as early as May 15, 2008. (Year: 2008).

Partial File Directory from JJS Technical Services, Inc. Listing Document Uploads at least as early as May 15, 2008.

International Search Report and Written Opinion of International Searching Authority for PCT/US2020/049937, ISA/RU, Moscow, Russia, dated Nov. 26, 2020.

Vaquerizo-Hdez et al., "A Low Power Consumption Algorithm for Efficient Energy Consumption in ZigBee Motes", Intelligent Systems Group, Computer Engineering Department, Universidad de Alcala; Sensors: MDPI, Aug. 19, 2017.

* cited by examiner

FIG. 6

Device Calibration

▲ Change Calibration Parameters for: TEMPERATURE_F on SN:00BAF5BB connected to WBR 00BAE764

Last Read [771] minus [0] scale by [1.000] plus [-30] plus [0] = [741]   Save

Term 1   Slope   Term 2   Offset   Adjusted   Comment

| Date | Status | Term 1 | Slope | Term 2 | Offset | Offset Comment | User |
|---|---|---|---|---|---|---|---|
| 2020-07-03 15:12:04 | Collected | 0 | 1.000 | -30 | 0 | null | |
| 2020-07-03 15:06:22 | Adjusted 2020-07-03 15:11:19 | 0 | 1.000 | -30 | 0 | reset it | fableson@iescorp.us |
| 2020-07-03 13:52:03 | Collected | 0 | 1.000 | -30 | -80 | null | |
| 2020-07-03 13:45:30 | Adjusted 2020-07-03 13:51:16 | 0 | 1.000 | -30 | -80 | down eight | fableson@iescorp.us |
| 2020-07-03 13:37:03 | Collected | 0 | 1.000 | -30 | 50 | null | |
| 2020-07-03 13:31:13 | Adjusted 2020-07-03 13:36:17 | 0 | 1.000 | -30 | 50 | bump + 5 | fableson@iescorp.us |
| 2020-07-02 22:51:03 | Collected | 0 | 1.000 | -30 | 0 | null | |

Fig. 7a

SYSTEM AND METHOD FOR ASSURING BUILDING AIR QUALITY

CROSS-REFERENCE TO RELATED APPLICATIONS

This application claims the benefit of U.S. Provisional Application No. 62/898,248 filed on Sep. 10, 2019, the contents of which are hereby incorporated by reference.

TECHNICAL FIELD

The present disclosure relates generally to energy management and, more particularly, to management of devices for environmental control of commercial and industrial buildings.

BACKGROUND

While certain improvements in building materials, construction techniques, and electronic systems provide for improved efficiency in operation of a building, energy costs remain among a building operator's greatest expenses. Energy costs, such as those costs arising from heating or cooling a building, may vary greatly based on factors such as resident or tenant environmental preferences, demand-based energy pricing, environmental conditions, and the like. Further, building operators may wish to provide for the comfort of tenants and residents, in addition to cost-optimization, creating a complex balance of energy costs and building requirements, a balance which legacy systems may be ill-equipped to resolve.

Legacy building management systems may provide for the collection of data relating to building environmental conditions. Further, such legacy systems may include features providing for control of building conditions using devices such as thermostat-linked heating and cooling systems, remote shutoffs for conduits, and the like. While such legacy systems may provide for environmental control and data collection, legacy means may be ill-suited to high-volume data processing and may lack certain connectivity features useful in reducing operator workload and maintenance.

In addition to the inefficiencies of legacy systems in managing high-volume building data, such systems may fail to provide certain modern functionalities necessary for efficient building environmental system management. Legacy systems may lack cloud-processing systems which provide for collection and analysis of large volumes of building data. Further, legacy systems may lack the interconnectivity required to collect energy market and grid data and to respond to such data automatically. In addition, legacy systems may require manual calibration and re-calibration of sensor and regulator devices, where manual calibration and re-calibration may require a prohibitively large outlay of time and effort on the part of building management and maintenance teams.

Further, legacy systems may fail to provide for management of building wellness controls. Building wellness controls include those controls concerning health and wellness parameters of building management, such as air filter status, drinking water contamination, and the like, as opposed to comfort controls which may be directed to provision of comfortable conditions for building occupants, such as controls directed to air temperatures. Further, legacy systems may require various trade-offs between wellness, comfort, and energy efficiency in order to reach various building management goals. As a result, legacy systems may lack the capacity to provide optimized wellness, comfort, and energy solutions, requiring intensive manual adjustment of wellness, comfort, and energy parameters to reach desired building control states.

In addition to legacy building management systems, certain smaller-scale comfort and energy management systems may provide similar functionalities in smaller-scope applications, such as homes, small offices, and the like. While smaller-scale systems provide for certain energy and comfort control functionalities, such systems lack the scope of application required to provide centrally-managed control of wellness, comfort, and energy needs for a large number of buildings, and larger buildings such as office towers, retail stores, and the like, as such buildings may include large numbers of management devices, complex connectivity architectures, predefined communication protocols, and the like. Further, smaller-scale systems may be primarily directed to management of comfort and energy parameters, to the exclusion of integrated safety and wellness controls. As a result, smaller-scale management systems may fail to provide functionalities and scopes of application required for use in large-scale building systems management applications.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for centrally assuring building air quality. The method comprises: collecting, from a set of sensors of a plurality of sensors, at least air quality data, wherein the plurality of sensors are installed in different locations within a building; analyzing the collected air quality data to determine an air-quality level across different locations within the building; determining whether an adjustment to at least one control device is required, wherein the determination is based on the determined air-quality level and at least one energy-consumption parameter; and actuating at least one building control device when an adjustment is required, wherein actuating at least one building control device allows for control of air quality across different locations within the building.

Certain embodiments disclosed herein also include a non-transitory computer readable medium having stored thereon causing a processing circuitry to execute a process for centrally assuring building air quality, the process comprising: collecting, from a set of sensors of a plurality of sensors, at least air quality data, wherein the plurality of sensors are installed in different locations within a building; analyzing the collected air quality data to determine an air-quality level across different locations within the building; determining whether an adjustment to at least one control device is required, wherein the determination is based on the determined air-quality level and at least one energy-consumption parameter; and actuating at least one building control device when an adjustment is required, wherein actuating at least one building control device allows for control of air quality across different locations within the building.

Certain embodiments disclosed herein also include a system for centrally assuring building air quality. The system comprises: a processing circuitry; and a memory, the memory containing instructions that, when executed by the processing circuitry, configure the system to: collect, from a set of sensors of a plurality of sensors, at least air quality data, wherein the plurality of sensors are installed in different locations within a building; analyze the collected air quality data to determine an air-quality level across different locations within the building; determine whether an adjustment to at least one control device is required, wherein the determination is based on the determined air-quality level and at least one energy-consumption parameter; and actuate at least one building control device when an adjustment is required, wherein actuating at least one building control device allows for control of air quality across different locations within the building.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

FIG. 6 is an illustration depicting a platform for managing register references, according to an embodiment.

FIG. 7a is an illustration depicting a configuration management platform, according to an embodiment.

DETAILED DESCRIPTION

Figure 1:
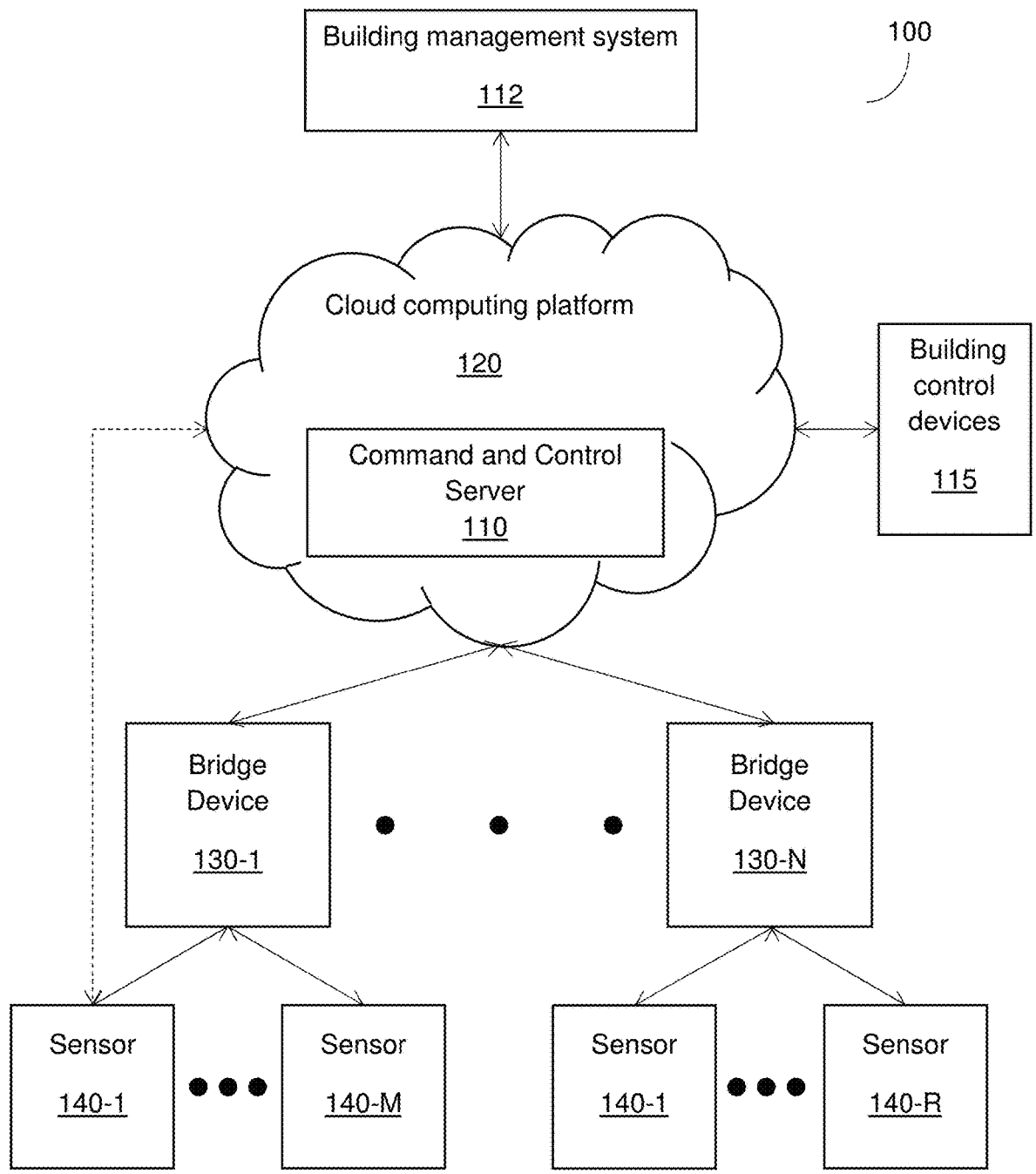
FIG. 1 is a network diagram utilized to describe a system for controlling building air quality and energy management devices, according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

FIG. 1 is an example network system 100 depicting the various embodiments for assuring building air quality, according to an embodiment. A network system 100 may include one or more components such as, as examples and without limitation, a command and control server (CCS) 110, included in a cloud computing platform 120, a building management system 112, one or more building control devices 115, one or more bridge devices 130-1 through 130-N (hereinafter, "bridge device" 130 or "bridge devices" 130), as well as one or more sensors 140-1 through 140-M (hereinafter, "sensor" 140). In an embodiment, a bridge device 130 may be configured to include features of one or more sensor devices.

The CCS 110, included in the cloud computing platform 120, provides for cloud-level administration of one or more bridge devices 130. As described hereinbelow, CCS 110 cloud integration may provide for large-scale sensor 140 data analysis and aggregation, where legacy building management systems (BMS) 112 may lack the scale or processing power required to perform such analyses. The CCS 110 may be configured to communicate with one or more components of the network system 100 via various devices' connections to the cloud computing platform 120, according to the means described hereinbelow.

Further, the CCS 110 may be configured to execute one or more of the methods or processes described hereinbelow, including execution of various data processing methods and routines to allow for centrally controlling at least air-quality, wellness and comfort in a building while factoring energy consumption. The management of CCS 110 data is described with respect to FIG. 2, below, and a hardware configuration of the CCS 110, according to an embodiment, is described with respect to FIG. 8, below. As described with respect to FIG. 8, below, the CCS 110 may include various processing, memory, and networking components, and the like, allowing the CCS 110 to execute instructions and provide data processing. The CCS 110 may be implemented as physical hardware, as software virtualizing physical hardware, or as a combination of physical and virtualized components.

According to the disclosed embodiments, the CCS 110 may be configured to execute instructions, and process data, for controlling building wellness, comfort, and energy management devices for assuring building air quality. Building wellness, comfort, air-quality and energy management devices may be building control devices 115, bridge devices 130, sensors 140, other, like, devices, and any combination thereof, some or all of which may be configured to provide functionality pertaining to building air quality. The CCS 110 may be configured to execute instructions and process data relevant to the various bridge devices 130 and sensors 140 via connections to the various devices according to various pre-defined communication protocols, patterns, exchange systems, and the like, including via various devices' connections to the cloud computing platform 120, as described hereinabove. In an embodiment, the CCS 110 may be configured to operate as a data upload server (DUS), as described hereinbelow.

In an example embodiment, CCS 110 may be configured to centrally control the plurality of bridge devices 130. As will be discussed in greater detail below, the CCS 110 may be configured to receive a request from each bridge device 130 to process, by the command and control server (CCS), at least a bridge update request. The update request may include, for example, a request to change any building parameter regarding air quality, wellness, comfort, energy, and the like, which may be pushed to the bridge devices 130, as described hereinbelow, to be subsequently relayed to the sensors 140. In an embodiment, the CCS 110 is configured to process such requests, to collect data from the one or more data stores, where the collected data may include, without limitation, at least code and configuration data, and to push the collected code and configuration data to the bridge devices 130. It should be noted that, in some embodiments, the CCS 110 may be configured to initiate a request to update the bridges. The CCS 110 may be further configured to collect data features from the bridge devices 130, and to process and archive the collected data features.

In certain embodiments, as described hereinbelow, the CCS 110 may be configured to integrate with legacy building management systems (BMS), such as, as examples and without limitation, BACNet, Modbus, and the like, and to integrate with cloud systems, online data sources, various peripherals, and the like, providing feature integration where such legacy building management systems may lack the described connective functionality. Such connectivity may provide for increased functionality of the CCS 110 to include management of legacy building management systems and the integration of modern and legacy systems.

In yet another embodiment, the CCS 110 may be configured to coordinate data collection from the sensors 140. In addition to collecting data from the bridge devices 130 and sensors 140, the CCS 110 provides collection schedules or routines for collection of data from large numbers of devices in particular orders. Custom collection routines may provide for enhanced processing of collected data by consideration of the order of collection. As an example, collecting data from smoke detectors at various positions in a building, according to certain schedules, could allow for the analysis and mapping of the spread of smoke within the building.

The CCS 110 may be deployed outside of a building and connected to building systems through a network. For example, the CCS 110 may be deployed in a cloud computing platform. It should be noted that such deployment may provide for CCS 110 monitoring of in-building device status to determine whether the building, or certain sections thereof, have problems such as loss of power. Further, off-site deployment, e.g., in a cloud platform, may provide for management of bridge devices 130, sensors 140, and the like, where environmental changes may occur. For example, when hazardous conditions arise, such as a need for remote adjustment of a hospital's ventilation systems when dangerous concentrations of a disease are detected in the air, remote deployment of the CCS 110 may provide for operator safety in updating the ventilation systems. As another example, hazardous conditions may also be detected when monitoring the grid or external conditions, such as weather stations which may inform the platform on external conditions which impact local building operation.

In an embodiment, a network system 100 may include a data upload server (not pictured). The data upload server (DUS) is a cloud-level server providing for collection and storage of data from one or more bridge devices 130, other, like, devices, or any combination thereof. The DUS may include one or more storage or memory components, such as a time series database (not shown), and the like. The time series database may be configured to store data received or collected according to the methods described hereinbelow, as well as other, like, methods. Data stored in the DUS, including data stored in the time series database, may be encrypted, unencrypted, or partially-encrypted. Further, stored data may be compressed to various degrees and may be stored to one or more physical partitions or other, like, separated storage allocations. The DUS, and any sub-component thereof, may be implemented as physical hardware, as software virtualizing physical hardware, or as a combination of physical and virtualized components. Further, the DUS may be interconnected with the various components of the network system 100, via connection with, or inclusion in, the cloud computing platform 120, according to the various means described hereinbelow.

The cloud computing platform 120 provides interconnectivity between the various components of the network system 100 and the CCS 110. The cloud computing platform 120 may be an on-premises system, a remote system, or a hybrid system including both local and remote aspects. The cloud computing platform 120 may be configured to connect with the various components of the network system 100 via connections including, without limitation wireless, cellular, or wired connections, local area network (LAN) connections, wide area network (WAN) connections, metro area network (MAN) connections, the Internet, the worldwide web (WWW), and the like, as well as any combination thereof. The cloud computing platform 120 may be a fully-physical network, hosted from dedicated or partitioned physical hardware, a fully-virtual network, including only virtualized components, or a hybrid physical-virtual network, including both physical and virtualized components. Further, the cloud computing platform 120 may be configured to provide for encryption of data, both at rest and in motion, and communication of encrypted, unencrypted, or partially-encrypted data. The cloud computing platform 120 may be a dedicated system, constructed and operated only for the purposes described herein, a shared-processing system, such as a cloud system hosted and operated by a cloud services provider, such as Amazon® Web Services, Microsoft® Azure, and the like.

The building management system (BMS) 112 is a dedicated control system providing for management and administration of various aspects of building air quality, comfort, wellness, energy management, and the like. The BMS 112 may be a pre-configured system implemented via one or more standards including, as examples and without limitation, ModBus, BACNet, and the like, as well as any combination thereof. The BMS 112 may provide for system connectivity via one or more communication protocols including, as examples and without limitation, Modbus TCP, Modbus RTU, BACNet IP, BACNet MSTP, and the like, as well as any combination thereof, for each of which the cloud computing platform 120 and CCS 110 may be likewise configured.

The BMS 112 may be configured to provide for building management functionalities including, as examples and without limitation, monitoring of various building sensors, other than the sensors 140, actuation of one or more building control devices 115, automating or scheduling building tasks or services, such as ventilation system purges and boiler pre-heating, and the like, as well as any combination thereof. In an embodiment, the BMS 112 may be directly connected to the building control devices 115 via means other than those described with respect to the cloud computing platform 120. In a further embodiment, the BMS 112 and building control devices 115, described hereinbelow, may be configured as a single, combined feature, a combination wherein the BMS 112 includes the building control devices 115, and vice versa, and the like.

The building control devices 115 are devices configured to provide for system-level control of various aspects of building air quality, comfort, wellness, and energy use, such as devices regulating temperatures, humidity, airflow, and the like. Building control devices 115 may include, as examples and without limitation, airflow control valves, air conditioners, furnaces and boilers, and other, like, devices. The building control devices 115 may be connected to the cloud computing platform 120 via one or more means or protocols, including those described with respect to the BMS 112. The building control devices 115 may be configured to actuate or otherwise engage based on one or more received instructions, including in binary modes of operation, such as on-off operation for a conduit flow valve, and in variable operation modes, such as may be used to provide increasing natural gas flow to a boiler, from a set start point to a set end point, for a given time period.

The bridge devices 130 are devices configured to serve as intermediaries between the sensors 140 and the various components of the network system 100. The bridge devices 130 may be configured to, as examples and without limitation, collect data from various sensors 140, to upload or push instructions to the various sensors 140, to upload or push collected data to the various components of the network system 100, to collect, from the various components of the network system 100, various instructions, to collect data, independent of the various sensors 140, to execute instructions, and the like, as well as any combination thereof. In some configurations, the bridge devices 130 are optional. In such configurations, some or all of the sensors 140 may communicate directly with the CCS 110 via those communicative means described herein.

In yet another embodiment, the bridge devices 130 may be configured to connect with the various components of the network system 100 via the cloud computing platform 120, according to the connective means described with respect thereto. Further, the bridge devices 130 may be configured to connect with the various sensors 140 via wired or wireless means, or any combination thereof, such as those described hereinabove, via those protocols described with respect to the cloud computing platform 120, as well as other, like, protocols, or any combination thereof. In addition, the bridge devices 130 may be configured to encrypt data, both at rest and in motion, and to transmit data with varying degrees of encryption.

In an embodiment, the CCS 110, via the cloud computing platform 120, may be configured to connect directly with the various sensors 140, without communication through the bridge devices 130. Where the CCS 110, via the cloud computing platform 120, is configured to so communicate with the sensors 140, the CCS 110, cloud computing platform 120, and sensors 140 may be configured to communicate via those means described hereinabove, other, like, means, and any combination thereof.

The sensors 140 are devices configured to gather data or signals later utilized for controlling building air quality, wellness, comfort, energy management, and the like, as well as any combination thereof. The sensors 140 may be devices such as, as examples and without limitation, thermometers, configured to measure air temperatures, particulate and gas detectors or sensors, configured to measure concentrations of various particulates, as well as gasses such as carbon dioxide ($CO_2$), hygrometers, configured to measure humidity, air pressure sensors, Ozone sensors, light sensors, gas sensors, TVOC sensors, barometric pressure sensors, and differential pressure sensors, and other, like, devices. Further, sensors 140, may be configured to collect data and to transmit collected data to the various components of the network system 100 via the bridge devices 130, to execute instructions received, via the bridge devices 130, from the various components of the network system 100, to execute other, like, functions, as well as any combination thereof. The sensors 140 may be configured to connect with the bridge devices 130 via those means described hereinabove. In an embodiment, as described hereinabove, the sensors 140 may be configured to connect directly with the CCS 110, via the cloud computing platform 120.

Sensors 140 may be disposed throughout one or more buildings to provide data regarding air quality, comfort, wellness, energy management, and the like, at scales including, as examples and without limitation, room-level, floor level, building level, and the like. In an embodiment, sensors 140, as may be included in a network system 100, may be disposed at various points throughout a building, including in configurations wherein multiple sensors of the same type are disposed in the same room or area, providing for sensor redundancy and error-checking. Where multiple sensors are deployed in the same or nearby rooms, areas, or the like, the CCS 110 may, when one or more sensor 140 defects are detected, subsequently configure neighboring sensors to assume the detection role of the defective sensor, including by interpolating conditions at the point of the defective sensor 140 based on data collected from nearby sensors 140.

In some embodiments, the CCS 110 is configured to assure air quality in a building. To this end, the CCS 110 is configured to receive or collect data, from a plurality of sensors, related to air quality. The collected data is then analyzed to determine a comfort air-quality level across different locations within the building. The CCS 110 is further configured to determine whether an adjustment to building control devices 115 is required, where the determination is based on the air-quality level rule and at least one energy-consumption parameter. The parameter may determine before-and-after energy consumption, or the energy-consumption before the adjustment and after the adjustment, if performed. This energy-consumption parameter is later compared to an energy-consumption rule to ensure that the cost associated with such changes does not exceed, for example, an allowed budget. The CCS 110 is configured to actuate one or more building control devices 115 through the BMS 112 when the adjustment is required.

It should be noted that centrally controlling air quality and comfort in a building ensures that any local independent control of the building control devices 115 may be overridden based on a central control. Further, considering energy-consumption parameters and rules ensures that any changes will be within the allowed budget or power usage. An embodiment for controlling the air quality and wellness are further discussed in FIG. 3.

Figure 2:
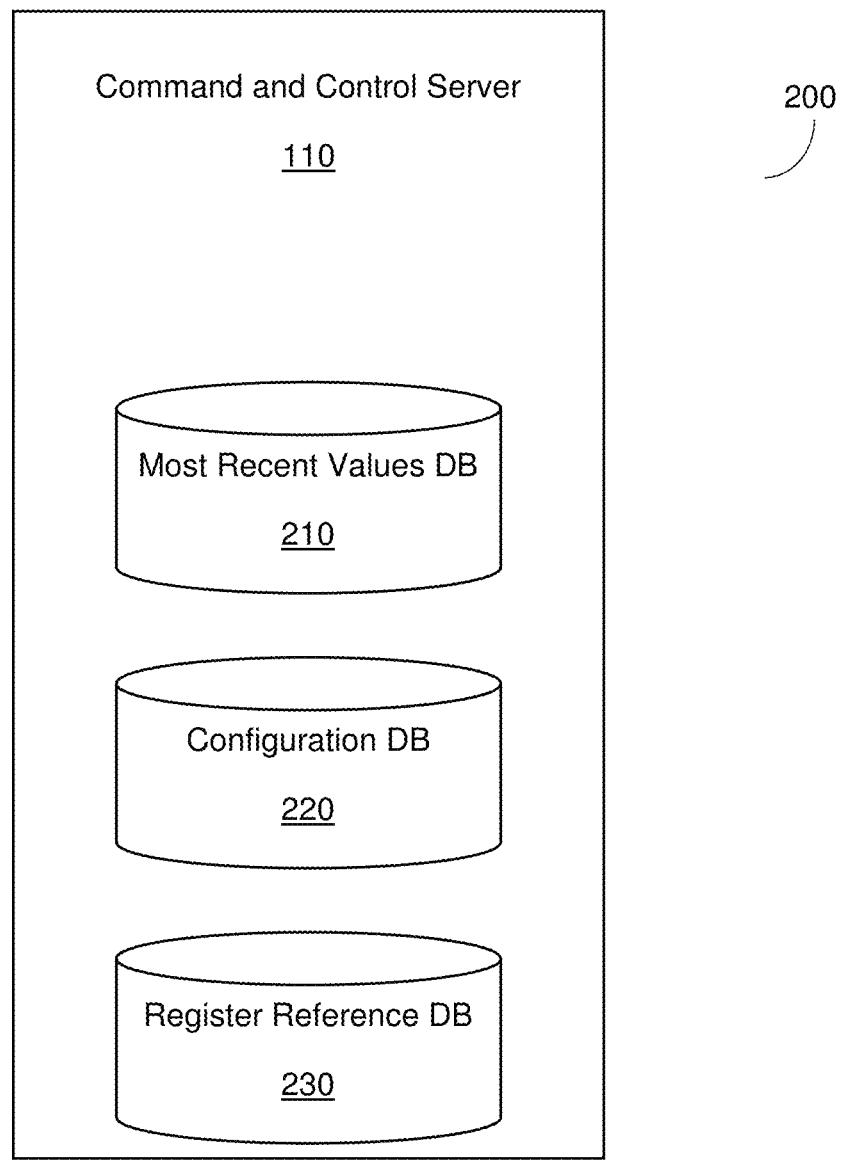
FIG. 2 is a system diagram of data management components of a command and control server, according to an embodiment.

FIG. 2 is an example functional diagram 200 of data management components of the CCS 110, according to an embodiment. The CCS 110, as described hereabove, may include various storage or memory components applicable to the temporary, semi-permanent, or permanent storage of data collected or generated according to the processes described herein, as well as other, like, processes.

The CCS 110 may include a most recent values database 210, a configuration database 220, a register reference database 230, other, like, databases, and any combination thereof. While the most recent values database 210, configuration database 220, and register reference database 230 are depicted as included in the CCS 110 for purposes of simplicity, it may be understood that the various databases 210 through 230 may be accessibly connected with the CCS 110, including through a network, where, in the network diagram 100 of FIG. 1, above, such connectivity is provided through the cloud computing system, 120, without loss of generality or departure from the scope of the disclosure. Further, data stored in the various databases 210 through 230 may be compressed or decompressed to various degrees, including by the databases 210 through 230, and may be encrypted, unencrypted, or partially-encrypted, including by the databases 210 through 230.

The most recent values database 210 provides storage for register data, as may be collected according to the processes hereinbelow, organized by order of receipt. Registers may include data features describing, variously, device and component operating systems, device-specific data features, user-defined features, and the like. Register data may include data relating to the operating system or systems of various components of a network system, such as the network system, 100, of FIG. 1, above.

In addition, register data may include data relating to the operation of various components of a network system, describing component-specific data features, such as, as an example and without limitation, the firmware version of a specific sensor. Further, register data may include user register data, where user register data is data relevant to a user's custom purpose. As an example, user register data may include custom-generated instruction sets for personalizing sensor device data output formats.

The configuration database 220 provides storage for device and system configuration instructions and collected data. Data which may be stored in the configuration database 220 includes, as examples and without limitation, sensor calibration data, building management system interface data, updated code images, various factory commands, DUS assignments, market and environmental data, register updates, device-specific commands, other, like, data, and any combination thereof. Data relevant to such a configuration database 220, and an interface for management thereof, is further described with respect to FIG. 7a, below. Further, similar data, relevant to management of the various systems and components described herein, generally, and an interface for management thereof, is described with respect to FIG. 7b, below.

The register reference database 230 provides storage for definitions of various registers. Registers, as described hereabove, are data features, describing various aspects of the components of the network system and the functionalities thereof. Register definitions may be organized according to device type, such as by assigning a value of "one" for a first type of sensor device and a value of "two" for a second sensor device, as well as by register definition version number or date. Further, device type and version values may be stored as eight-bit values.

In an embodiment, the register reference database 230 may be configured as a relational database, providing applicability of stored definitions for purposes including user interface (UI) enhancement, toolchain automation, application programming interface (API) generation and documentation, other, like, purposes, and any combination thereof. The register reference database 230, and the organization and contents thereof, are described in detail with respect to FIG. 6, below.

Figure 3:
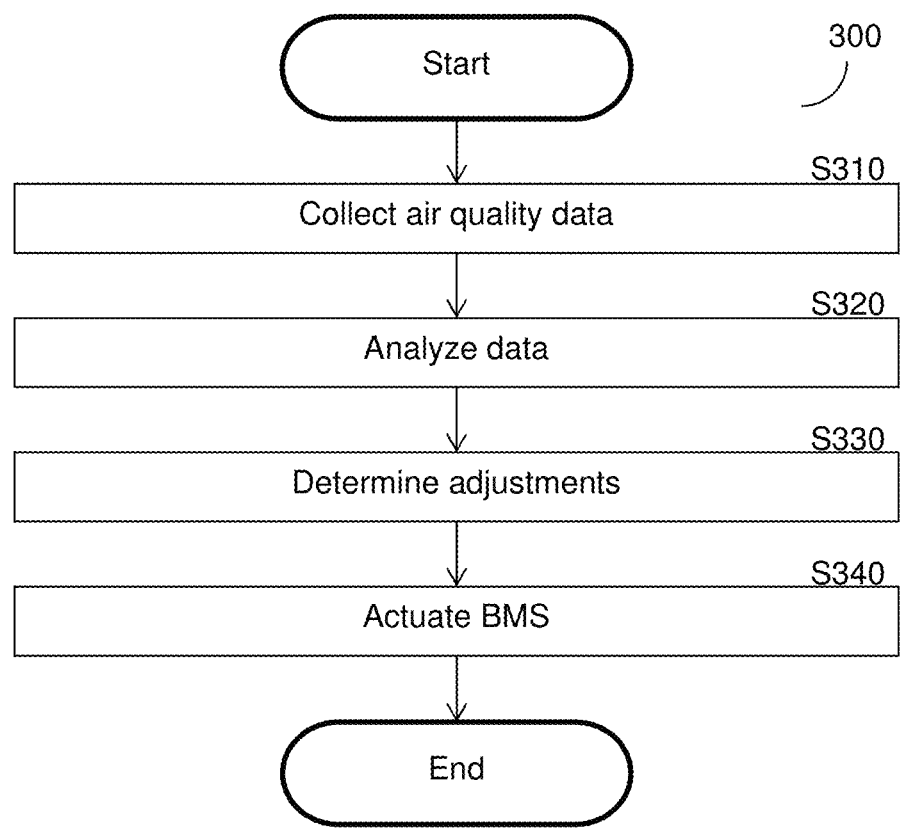
FIG. 3 is a flowchart depicting a method for assuring building air quality, according to an embodiment.

FIG. 3 is an example flowchart depicting a method for assuring building air quality, according to an embodiment. A method for assuring building air quality, as described hereinbelow, as well as other, like, processes, may be executed by one or more command and control servers such as, as examples and without limitation, the CCS, 110, of FIG. 1, above, and the like, where such systems or platforms may be deployed in one or more cloud computing platforms such as, as examples and without limitation, the cloud computing platform, 120, of FIG. 1, above.

At S310, air quality data is collected. Air quality data is data describing one or more aspects of building air, ventilation, and the like. Measurements which may be included in air quality data, collected at S310, include, as examples and without limitation, temperature, pressure, relative humidity, airflow speeds, particulate concentrations, gas concentrations, other, like, measurements, and any combination thereof. Air quality data may be collected by a command and control server, such as the CCS, 110, of FIG. 1, above, from one or more devices including, without limitation, the bridge devices, 130, of FIG. 1, above, the sensors, 140, of FIG. 1, above, other, like devices, and any combination thereof. The sensors, 140, of FIG. 1, above, may be connected to one or more bridge devices, 130, of FIG. 1, above, where, as described with respect to FIG. 1, the bridge devices, 130, may be configured to provide connectivity between a server providing central control and connectivity with at least one building control device, and the sensors. The collected air quality data may be stored, temporarily or permanently, in one or more memory or storage components, including, without limitation, the components included in the network system, 100, of FIG. 1, above, various sub-components thereof, and the like, as well as any combination thereof.

At S320, air quality data is analyzed. Air quality data may be analyzed by application of one or more algorithms, methods, or other, like operations. Air quality data analysis at S320 may include the identification of patterns, trends, gradients, outlier values, and the like, as well as any combination thereof. Analysis of air quality data at S320 may include instantaneous analysis, providing for analysis of data at the instant of collection, short-term analysis, providing for analysis of data for a short period prior to collection, such as data from a previous hour or day, and the like, and long-term analysis, providing for analysis of data over longer periods, including through the first collected datapoint. Further, analysis of air quality data at S320 may include other, like, analysis paradigms, as well as any combination thereof. In addition, analysis of air quality data at S320 may further include analysis according to one or more pre-defined or user-defined analysis methods, providing for isolation of particular datapoints, trends, and the like, and reduction of analytic processing load. Further, air quality data analysis at S320 may include analysis of collected data to identify one or more air quality metrics concerning air-quality levels, wellness levels, energy consumption, and the like, as well as any combination thereof.

At S330, adjustments are determined. Adjustments may be calculated changes to building air quality conditions, calculated to drive air quality measurements to levels within given parameters, such as air-quality levels, wellness parameters, energy consumption parameters, and the like, including calculated changes to building control devices, as may be applied at S340, below. Adjustments may be determined according to one or more pre-defined or user-defined building management system rules. Building management system rules may be thresholds, limits, ranges, and the like, defining various air quality targets. Building management system rules may be configured to provide for building air quality, comfort, wellness, energy consumption, and the like, reflecting various requirements and preferences of interested parties including building operators, managers, and owners, various tenants and occupants, regulatory bodies, and the like. A first example of a building management system rule may be a rule specifying that, when a building is occupied, the carbon dioxide concentration in each room must be below a certain level. A second example of a building management system rule may be a rule specifying that when a building is in a low-or-no occupancy state, such as at night, in the case of an office building, building air temperature is to be maintained within a range different than that applied to full-occupancy cases.

Energy consumption rules, as may be included in one or more BMS rules, such as those described hereinabove, may be rules regarding building energy usage. Energy consumption rules may include rules defining, as examples and without limitation, maximum single-instant energy consumption, maximum time-period energy consumption levels, such as daily, weekly, and monthly maximum levels, maximum consumed energy costs, and the like, as well as any combination thereof. Further, energy consumption rules may be configured to include limits, maximum levels, and the like, which may be variably adjusted or pre-assigned for different hours of the day, such as rules specifying different maximum energy consumption levels for an hour in the middle of the day, as opposed to an hour period in the middle of the night. In addition, adjustments determined, at S330, based on one or more energy consumption rules, may be determined, at S330, and subsequently applied, at S340, to account for energy consumption requirements of the determined adjustments, wherein such energy consumption requirements may be determined, at S330, to satisfy the one or more energy consumption rules.

Adjustments determined at S330 may include adjustments calculated to achieve local air quality, comfort, wellness, energy management, and other goals specified by individual users through various room-level or floor-level systems. Where a user interacts with such a system to express a preferences, such as by setting a preferred temperature on a thermostat, such set-points may be aggregated to identify compromises which serve the local goals of the various users. Compromises may be identified via a variety of means including, without limitation, majority voting, such as by counting the number of set-points specifying various values and determining adjustments suited to the majority value selected, master control, wherein a given user's set-point may be configured to override other, local set-points, other, like, means, and any combination thereof. In a first example, where three neighboring offices each include thermostats, and where two of the three thermostats are set to seventy degrees while the third is set to sixty-five, a majority vote may be applied to determine an adjustment needed to raise or lower the temperature of the offices, the floor, or another sub-region of the building, to seventy degrees. In a second example, where the thermostat set to sixty-five degrees is specified as a master thermostat, using the same set-points, the seventy degree set-points may be overridden and the local temperature may be set to sixty-five degrees, with the necessary adjustments so determined.

Adjustments determined at S330 may include adjustments calculated to bring building air quality within the pre-defined or user-defined thresholds, limits, and ranges specified in the building management system rules, including by undertaking actions calculated to adjust building air quality. Adjustments calculated to adjust building air quality may include, as examples and without limitation, increasing or decreasing airflow rates to given rooms or floors, increasing or decreasing air temperatures, increasing or decreasing air filtration rates and requirements, and the like, as well as any combination thereof.

Where analysis at S320 includes the identification of a building air-quality level based on the data collected at S310, determination of adjustments at S330 may include comparison of the one or more identified building air-quality levels with one or more building air-quality level rules, such as may be included in a building management system rule, such as those described hereinabove. Further, where analysis at S320 includes identification of one or more energy consumption parameters, determination of adjustments at S330 may include comparison of the identified energy consumption parameters with one or more energy consumption parameter rules, such as may be included in a building management system rule, as described hereinabove. In addition, where both building air-quality levels and energy consumption parameters are identified at S320 and compared at S330, determination of adjustments at S330 may further include determination of one or more adjustments necessary to satisfy both energy consumption and air-quality level rules.

Determination of adjustments at S330 may include consideration of one or more data points or sets other than those collected at S310, analyzed at S320, or both, including data feeds collected from one or more cloud services. Where determination of adjustments at S330 includes determination based on such external data feeds, determination at S330 may further include receiving one or more data feeds from such cloud services. Such external datapoints and sets may include, as examples and without limitation, current and historic energy costs, weather forecasts, anticipated building occupancies, known device or system maintenance schedules, and the like, as well as any combination thereof. External datapoints and sets may be drawn from one or more sources including, without limitation, various internet sources, as may be accessible through a cloud computing platform, such as the cloud computing platform, 120, of FIG. 1, above, from other, like, sources, or any combination thereof. As an example, determination of adjustments at S330 may include the calculation of a building cooling schedule, as may be applicable to the actuation of air filtration systems at S340, below, based on collected predictions of high pollen counts for a given, future period.

In an embodiment, determination of adjustments at S330 may include generation of one or more building demand responses. Building demand responses may be pre-defined, user-defined, and/or adjustable rules concerning relationships between energy pricing and building air quality, comfort, and wellness. Such rules may be updated by a user or by the CCS based on data collected at S310 and analyzed at S320, external data, as described hereinabove, other, like, data, and any combination thereof. Building demand responses may be generated based on data including, without limitation, energy usage trends anticipated energy demands, based on historic use, anticipated energy pricing, determined similarly, energy consumption rules, other, like, data, and any combination thereof. Generated building demand responses may be configured to override one or more building management system rules, as described hereinabove, providing for energy conservation with allowable deviation from the ranges, thresholds, and the like specified in the over-ridden rule or rules. As an example, a building demand response may include a predicted energy cost, based on anticipated building energy use and predicted energy rates, which exceeds an operator's pre-determined energy cost threshold. In the same example, the building demand response may be configured to override a temperature range specified in a building management system rule, providing for energy savings by reducing building heating such that building air temperature falls outside the pre-determined range.

In some configurations, the adjustment is performed when at least one energy-consumption rule and at least one air-quality level rule and at least one energy-consumption parameter. The at least one wherein the energy-consumption rule is satisfied after factoring a certain level of energy consumption caused by the adjustment. Such certain level of energy consumption may include higher consumption or lower consumption of energy. In a further embodiment, the actuation is optimized based on the demand response.

At S340, building control devices and systems are actuated. Building control devices and systems may be actuated based on the one or more adjustments determined at S330, above, where such adjustments may be determined based on measured building conditions, pre-defined or user-defined air quality, comfort, wellness, and energy-management parameters, and the like, including adjustments determined to optimize the actuation of building control devices and systems based on one or more building demand responses, building management system rules, and the like, as well as any combination thereof. Building control devices and systems may be devices or systems included in a building management system (BMS), such as is described hereinabove. Where, at S330, one or more adjustments are determined to be necessary, actuation of BMS devices and systems at S340 may be configured to drive measured air quality parameters, across different locations in a building, to within the various ranges described hereinabove. BMS devices and systems may be actuators, regulators, controllers, and the like, configured to provide for direct control of building air quality, comfort, wellness, and energy management. As described with respect to the building control devices, 115, of FIG. 1, above, BMS devices and systems may be, as examples and without limitation, devices for regulating airflow, such as airflow control valves, devices for regulating air temperature, such as air conditioners and furnaces, devices for regulating humidity, such as humidifiers and dehumidifiers, and the like, as well as any combination thereof. BMS devices and systems may be configured for actuation in binary modes of operation, such as "open-close" operation for a flow control valve, as well as variable operation, such as a precise feed rate of natural gas into a heating furnace. As an example, based on that provided with respect to S330, above, building furnaces may be actuated at S340 by limiting natural gas feed rates to a level determined at S330, where the determined feed rates are calculated, at S330, to provide for heating to temperatures outside of a normal temperature range, based on a building demand response.

In an embodiment, steps S310 through S340 may be executed, sequentially, in a continuous process for monitoring and assuring air quality. Where the aforementioned steps are executed in a continuous, looping process, subsequent data collections and analyses may determine air quality, and the like, following the actuation of BMS devices and systems, and may, subsequently, be followed by further determinations and actuations, as described hereinabove. Such a looping process may provide for continuous monitoring and adjustment of building air quality, including based on changes detected by one or more sensor devices in response to prior BMS device and system actuations.

In some embodiments, the method discussed with reference to FIG. 3 can be utilized for actuating at least one building control device to improve wellness of occupants in the building, wherein the actuation for improving wellness is based at least on sensor readings related to air filter status and drinking water contamination.

Figure 4:
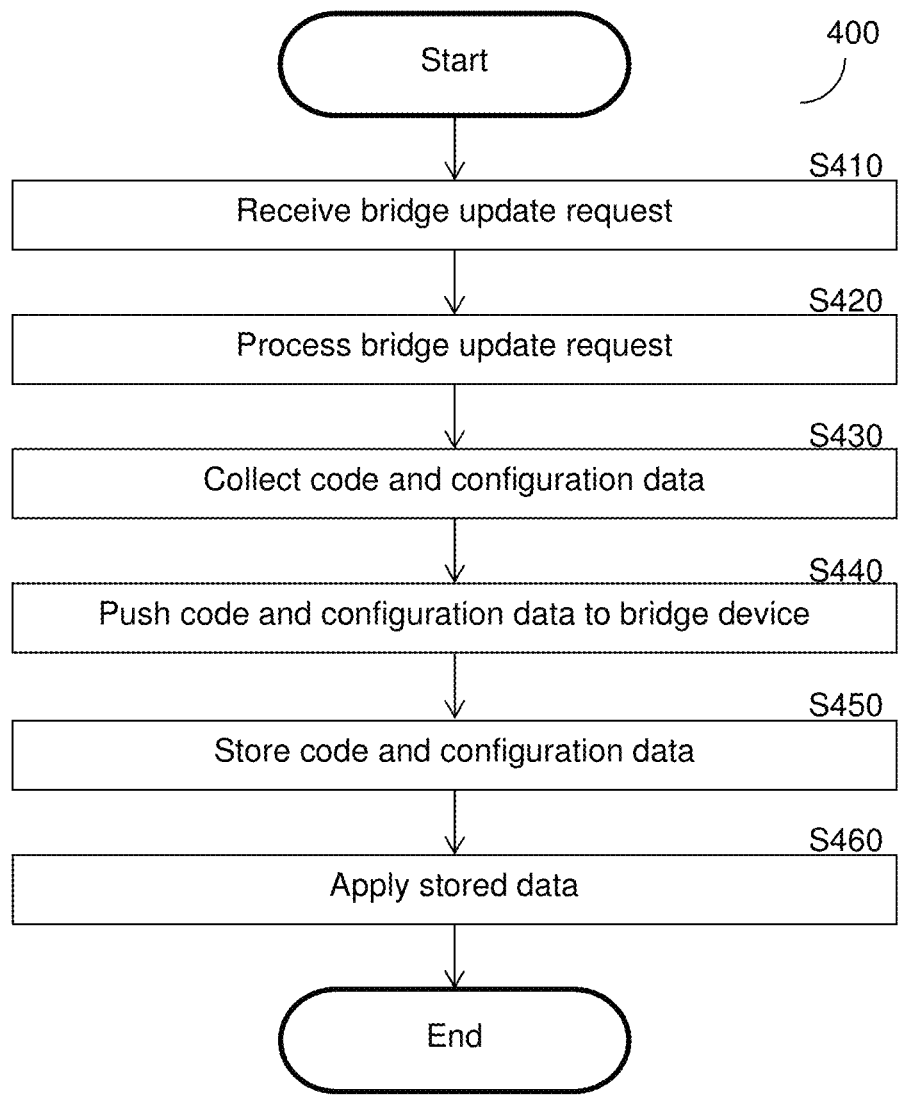
FIG. 4 is a flowchart depicting a method for updating one or more bridge devices, according to an embodiment.

FIG. 4 is an example flowchart 400 depicting a method for updating one or more bridge devices, according to an embodiment.

At S410, a bridge update request is received. A bridge update request is a command, script, instruction set, or other, like, data feature configured to initiate a process for updating one or more bridge devices. Processes for updating one or more bridge devices may include processes for updating bridge device functionality, including updates providing for custom data visualizations, custom sensor management schedules and operation modes, building-specific or user-specific hardware configurations, and the like. A bridge device update process may include propagation of one or more updates to bridge devices by transmission of firmware and other data features to devices with capabilities and functionalities matching the update or updates relevant to the bridge device update process. In an embodiment, a process for updating one or more bridge devices may include user or system roll-back of various updates, providing for automatic and manual control of update versions and corresponding functionalities.

A bridge update request, as received at S410, may be received by one or more devices or components of a system for controlling building wellness, comfort, and energy management devices, such as the system, 100, of FIG. 1, above, including, as an example, a command and control server (CCS), such as the CCS, 110, of FIG. 1, above, as well as other, like, devices or components. A bridge update request may include data features such as, as examples and without limitation, bridge update schedules, bridge device specifications, sensor device specifications, update request specifications, other, like, data features, and any combination thereof.

Receiving a bridge update request at S410 may include generating, via code executed on a CCS, a bridge update request. As described in the embodiments relevant to generation of a bridge update request by a bridge device, discussed below, a bridge update request generated by CCS-implemented code or instructions may be generated according to various user-defined or pre-defined schedules, such as, as examples and without limitation, weekly generation, daily generation, hourly generation, generation at five-minute intervals, and the like. Where a bridge update request is generated by a CCS employing bridge update request generation code at S410, the generated bridge update request may be subsequently processed, by execution of S420, without transmission of the generated update request via the network.

In an embodiment, a bridge update request may be generated by a bridge device, such as the bridge devices, 130, of FIG. 1, above. In a further embodiment, bridge update requests may be generated by bridge devices according to various user-defined or pre-defined schedules, such as, as examples and without limitation, weekly generation, daily generation, hourly generation, generation at five-minute intervals, and the like. In addition, bridge update requests may be generated by one or more bridge devices according to various other schedules or triggers including, without limitation, generation upon receipt of a triggering command from a sensor device, such as the sensors, 140, of FIG. 1, above, generation upon receipt of a user command through an interface included in the bridge device, by other, like, schedules and triggers, and any combination thereof. Where a bridge update request is generated by a bridge device, the generated bridge update request, the contents thereof, and any subsequent response transmissions, and the like, may be unique to the generating bridge device and may include one or more identifying data features describing the generating bridge device including, without limitation, a unique serial number assigned to or encoded in a specific bridge device, other, like, features, and any combination thereof.

At S420, a bridge update request, as received at S410, is processed. A bridge update request may be processed by the command and control server (CCS), 110, of FIG. 1, above, as well as other, like, processing components or devices, and any combination thereof. Processing a bridge update request at S420 may include, without limitation, identification of code images, data registers, other, like, resources, and any combination thereof which may be relevant to the received bridge update request. Identification of resources may include determination of the locations of various relevant resources within memory or storage components included in, or connected to, the CCS, including those memory or storage components connected to the CCS via the network system, 110, of FIG. 1, above.

In addition, identification of resources at S420 may include determination of one or more orders for resource transmission, such as during a push process, as described with respect to S440, below, where the one or more orders for resource transmission may be based on factors including, without limitation, administrator specification, file size, transmission schedules, dependencies between resources, other, like, factors, and any combination thereof.

Further, processing a bridge update request at S420 may include, without limitation, identification of one or more devices including, as examples and without limitation, the bridge devices, 130, and sensors, 140, of FIG. 1, above, as may be relevant to the received bridge update request. Identification of one or more relevant devices may include determination of bridge update request sources and resource destinations, as may be included in the bridge update request received at S410. Further, identification of one or more relevant bridge devices may include determination of network pathways, providing for optimized subsequent bridge update response timing and loading, including determination of minimum-hop CCS-to-target-bridge pathways, determination of lowest-latency CCS-to-target-bridge pathways, and the like, as well as any combination thereof.

At S430, code and configuration data are collected. Code and configuration data includes data relating to network system configuration, data relating to network system configuration changes, data relating to operation of one or more bridge or sensor devices including, without limitation, program code, custom graphics, updated operating system programming instructions, software or firmware updates, calibration instructions or commands, data pull requests, custom instructions, other, like, code and configuration data, and any combination thereof. Code and configuration data may be collected from one or more sources including, without limitation, a configuration database, such as the configuration database, 220, of FIG. 2, above.

At S440, code and configuration data are pushed to the bridge device. Code and configuration data, as collected at S430, may be pushed to the bridge device via one or more means including, without limitation, through the network connectivity provided by the cloud computing system, 120, of FIG. 1, above, via the means and protocols described with respect thereto. Code and configuration data pushed to the various bridge devices may be pushed via secured channels, including those secured by techniques including, without limitation, application of Secure Sockets Layer (SSL) protocols, and the like, as well as any combination thereof. Further, the code and configuration data pushed to the bridge device, including the various files, messages, and the like, included in the same code and data, may be compressed, encrypted, or both, to varying degrees. Further, transmissions generated during the execution of S440 may be subsequently stored, including by storage of one or more transmissions in a configuration database, such as the configuration database, 220, of FIG. 2, above, for application in subsequent auditing processes.

At S450, code and configuration data are stored. Code and configuration data, as pushed to the bridge device at S440, may be stored in one or more databases or repositories included in or otherwise connected to the bridge device to which code and configuration data are pushed. The databases or repositories storing the pushed code and configuration data may be compressed, encrypted, or both, to varying degrees, providing for ongoing confidentiality of pushed data and code, including data and code in transmission and at rest.

At S460, stored data is applied. Stored data may be the code and configuration data stored at S450, as well as other, like, data, and any combination thereof. Stored data may be applied for one or more purposes including, as examples and without limitation, updating firmware, application code, and the like, for one or more devices such as, as examples and without limitation, the various bridge and sensor devices described herein, as well as other, like, purposes. Stored data may be applied by one or more devices or components described herein including, without limitation, the CCS 110, bridge devices 130, and sensors 140, of FIG. 1, above.

In a first example, where stored data applied at S460 includes application code, and where the included application code is applied to a bridge device, such as the bridge devices, 130, of FIG. 1, above, the included application code may be written to one or more memory or storage components of the bridge device including, without limitation, Electronically Erasable Programmable Read-Only Memory (EEPROM), a secure digital (SD) card, and the like, as well as any combination thereof. In a second example, where stored data applied at S460 includes firmware for one or more bridge devices, such as the bridge devices, 130, of FIG. 1, above, application of stored data at S460 may include configuration of a flash writer, installed on or communicatively connected to, the bridge device, to retrieve data stored at S450 and, subsequently, to over-write application code, thereby effecting a self-replacement. In the same second example, a flash writer may be similar to a bootloader. Further, in a third example, where stored data applied at S460 includes firmware for one or more sensors, such as the sensors 140 of FIG. 1, above, application at S460 may include configuration of a flash writer, installed on or, communicatively connected with, a bridge device, to retrieve data stored at S450 and to over-write the application code, thereby effecting a self-replacement. As above, in the third example, a flash writer may be similar to a bootloader.

It may be understood that while the various examples provided hereinabove describe application of stored application code and firmware at S460 to bridge and sensor devices, the application of stored data at S460 may be equally applied to other types of stored data and other types of components or devices, including any combination thereof, without loss of generality or departure from the scope of the disclosure.

Figure 5:
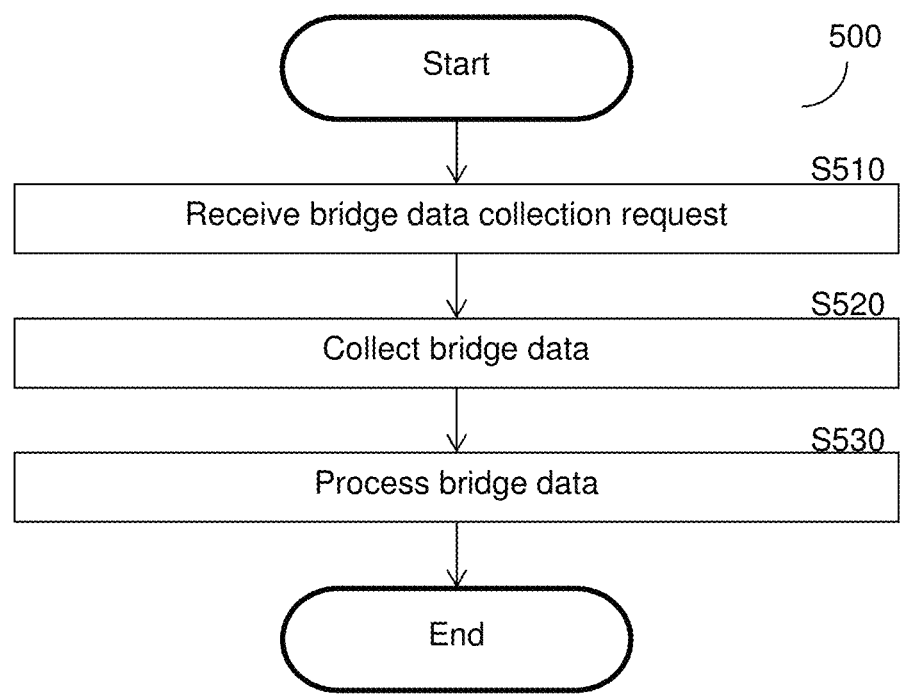
FIG. 5 is a flowchart depicting a method for collecting data from one or more bridge devices, according to an embodiment.

FIG. 5 is an example flowchart 500 depicting a method for collecting data from one or more bridge devices, according to an embodiment.

At S510, a bridge data collection request is received. A bridge data collection request is a command, script, instruction set, or other, like, data feature configured to initiate a process for collecting data from one or more bridge devices. A bridge data collection request may be received from one or more sources including, without limitation, the various components depicted in FIG. 1, above, other, like, components, and any combination thereof, via the connectivity provided by the cloud computing system, 120. In an embodiment, a bridge data collection request may be generated by a bridge device, such as the bridge devices, 130, of FIG. 1, above. A bridge data collection request may include data features such as, as examples and without limitation, bridge data collection schedules, bridge device specifications, data collection request specifications, other, like, data features, and any combination thereof.

At S520, bridge data is collected. Bridge data may include various operating system, device, and user registers, as described herein, as well as other, like, data features, and any combination thereof. Collected bridge device data features may be relevant to, without limitation, the operation of a bridge device, one or more sensors connected thereto, and the like, as well as any combination thereof. Bridge data may include data collected, generated, or processed by one or more bridge devices, sensor devices, other, like, devices, and any combination thereof. Bridge data may be collected from one or more bridge devices, including as specified in the bridge data collection request received at S510. Further, as specified by the bridge data collection request, collection of bridge data at S520 may include complete collection of all available data, as well as collection of limited data including only data meeting certain specifications defined in the request, such as, as examples and without limitation, data relevant to particular bridge or sensor devices, data relevant to particular time periods, data relevant to specific aspects of building energy, wellness, and comfort management, and the like, as well as any combination thereof. Further, collection of bridge data at S520 may be executed according to one or more pre-defined or user-defined collection schedules, triggering events, or both, as may be specified in the request. Examples of data collection schedules may include, as examples and without limitation, weekly collection, daily collection, hourly collection, collection at five-minute intervals, continuous collection, and other, like, schedules. Further, events triggering collection may include, as examples and without limitation, user entry of a data collection command, detection of anomalous environmental conditions by one or more devices, detection of device malfunctions, other, like, events, and any combination thereof.

Collected data features to be archived to one or more data upload servers may be encrypted to various degrees, both at rest and in motion, and may be organized within the respective bridge devices, including redundant organization by creation of data feature copies corresponding to each data upload server for which the data features are intended. In an embodiment, a bridge device, from which such data is collected, may be configured to accumulate bridge data up to the capacity of the bridge device's internal memory or storage components. As an example, such a bridge device may be configured to accumulate up to two weeks of data.

At S530, collected bridge data is processed. Collected bridge data may be processed by one or more components or devices including, without limitation, the command and control server (CCS), 110, of FIG. 1, above, as well as other, like, processing components or devices, and any combination thereof. Processing collected bridge data at S530 may include the application of one or more algorithms, methods, or other pre-defined or user-defined data processing or analysis procedures, and the like. Further, processing at S530 may include display, storage, and the like, as well as any combination thereof, of processed data, unprocessed data, and any combination thereof. Where processing at S530 includes storage, processed data, unprocessed data, and any combination thereof may be stored to one or more storage or memory components including, as examples and without limitation, storage or memory components included in, or connected to, the CCS, 110, of FIG. 1, above, to other, like, storage or memory components, and any combination thereof. Further, where bridge data processing at S530 includes display of processed data, unprocessed data, and any combination thereof, such a display may be provided through one or more user interfaces including, as examples and without limitation, those described with respect to FIGS. 7a and 7b, below.

Figure 6:
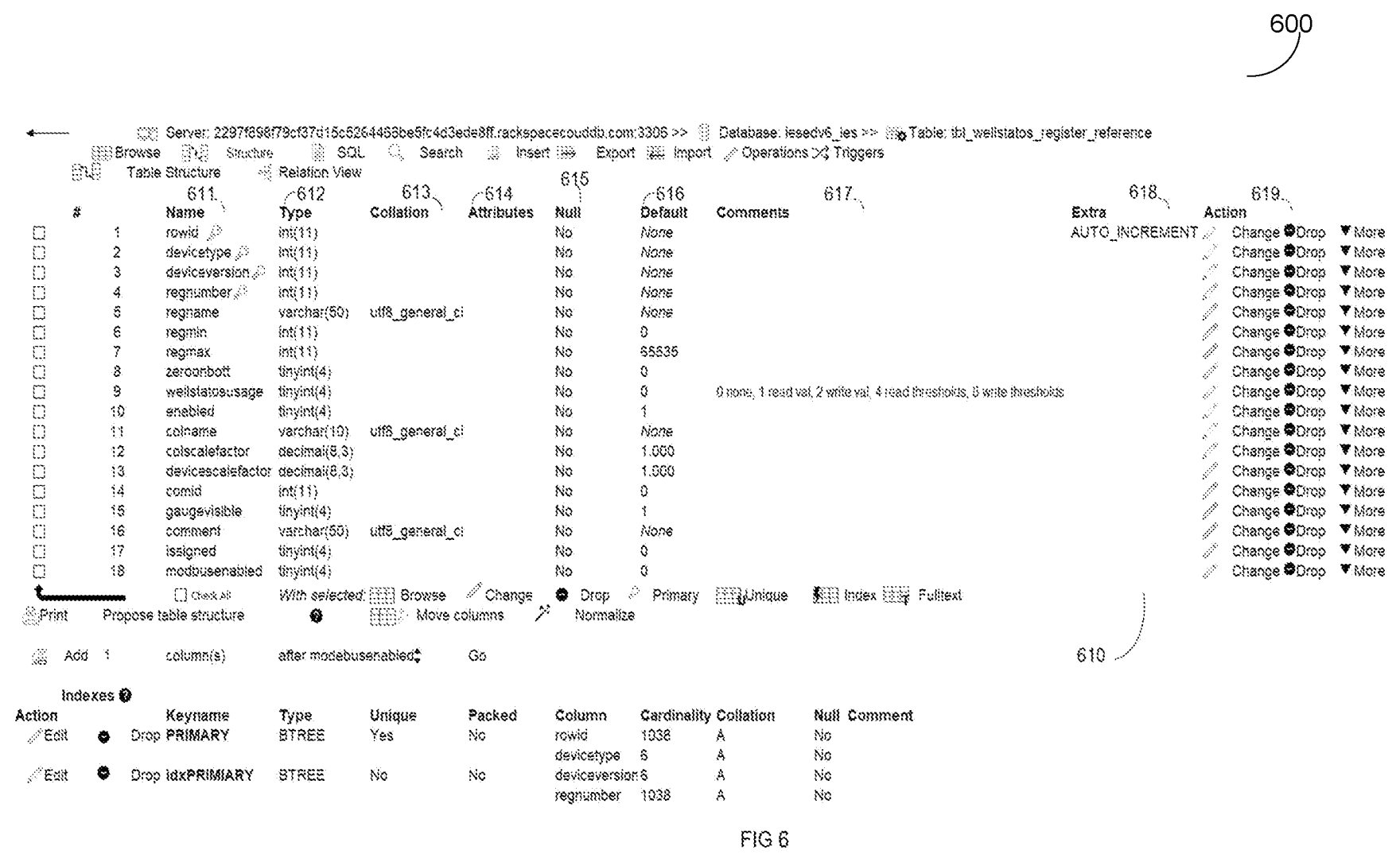

FIG. 6 is an illustration depicting a platform for managing register references 600, according to an embodiment. The platform for managing register references 600 may be applicable to management, review, organization, and the like, of one or more register reference databases, such as the register reference database, 230, of FIG. 2, above. Such a platform for managing register references 600 may be accessible through one or more user devices connected to a network, such as the network system, 100, of FIG. 1, above. User devices may include, as examples and without limitation, personal computers, smart phones, tablet computers, dedicated kiosks, and the like, as well as any combination thereof.

The platform for managing register references may include an entry review panel 610, wherein the entry review panel 610 may be configured to display information regarding one or more register entries. Register entries displayed through the review panel 610 may be categorized or labeled with one or more data features including, without limitation, entry names 611, entry types 612, such as integers, decimals, strings, and the like, collation entries 613, describing registers to which displayed registers may be collated, attribute descriptions 614, null entry indicators 615, register default values 616, custom comments 617, and extra register data features 618.

Other attributes which may be relevant to various registers include, without limitation, whether the register is persisted as time-series data, whether the register is modifiable, such as through read and write commands via the user interface, whether zero is a valid register value, respective register minimum and maximum values, scaling factors, register interpretations, and the like, as well as any combination thereof. Further, the review panel may include an action selector 619 for each register, providing for user selection of register change tools, register deletion tools, and the like.

FIG. 7a is an illustration depicting a configuration management user interface, according to an embodiment. The user interface 700 may be applicable to review, organization, and other management of configuration data, as may be applicable to configuring various bridge and sensor devices, as described herein. The user interface 700 may be accessible through one or more user devices connected to a network, such as the network system, 100, of FIG. 1, above. User devices may include, as examples and without limitation, personal computers, smart phones, tablet computers, dedicated kiosks, and the like, as well as any combination thereof. The configuration management platform may include reference information describing a configuration mode 705, a sub-mode 710 such as, as depicted in the illustration, configuration of Fahrenheit temperature calibration settings in a device calibration mode, a target sensor device 715, and an intermediate bridge device 720.

Further, the configuration management user interface 700 may include one or more configuration management selectors 725, which may be configured to collect, from user input, one or more values applicable to the creation or adjustment of various configuration settings including, in the example shown in the example illustration, a "last read" value, a "term one" value, a "slope" value, a "term two" value, an "offset" value, an "adjusted" value, and one or more comments. The configuration management user interface 700 may be configured to display one or more configuration management logs through the view panel 730, including configuration log entries including one or more of the parameters described hereinabove.

While the example illustration includes a configuration management user interface 700 operating in a "device calibration" mode 705, it may be understood that configuration management platforms 700 may operate in various modes including, as examples and without limitation, building management interface mode, code image update mode, reboot, restart, and factory reset modes, data upload server assignment mode, market and environmental data mode, register update mode, and the like, without loss of generality or departure from the scope of the disclosure.

Where a configuration management user interface 700 operates in sensor calibration mode, the management user interface 700 may be configured to provide for display and management of data relevant to configuration of sensors, bridge devices, or both. Operation in sensor calibration mode may provide for remote adjustment, calibration, or both, of various sensor and bridge devices. Calibration parameters may include, as examples and without limitation, base offset values, slope values, secondary offset values, sensor lot numbers, as may be applicable for persistent calibration independent of device location, as well as quality management, customer offset values, applicable to provide a custom offset for authorized end-users, and the like, as well as any combination thereof. Where a configuration management user interface 700 operates in sensor calibration mode, all entered calibration data changes may be audited, including changes initiated from both cloud systems and local systems and devices. Further, operation in sensor calibration mode may include sensor value reviews to identify and compensate for drift, providing for persistent sensor calibration.

Where a configuration management user interface 700 is in Building Management System (BMS) mode, the management user interface 700 may be configured to provide for adjustment of building management system interface parameters and methods.

In an embodiment, a building management system (BMS) mode is a mode of operation. The configuration management user interface 700 is configured to provide for collection of data from, and transmission of data, including instructions, commands, and the like, to legacy or other external building management systems, including by configuration of various components described herein, execution of various processes described herein, and the like, as well as any combination thereof.

Operation in BMS mode may include features providing for review and management of, for Modbus systems, BACNet systems, other, like, systems, and any combination thereof, system-device interface data transfer rates, communication port assignments, software-defined system and device identifications, server roles and permissions, such as read and write access, client roles and permissions, such as data transfer rates, identifiers, and remote register read and write permissions, and user and device register exchanges, as well as other, like, features, and any combination thereof.

Where a configuration management user interface 700 operates in Application Update mode, the management user interface 700 may be configured to provide for review and adjustment of code image update parameters and methods. In an embodiment, an application update mode is a mode of operation wherein a configuration management user interface 700 is configured to provide for over-the-air (OTA) updates of one or more code images, as well as code update parameters and methods, for various devices connected to a CCS via a network including, without limitation, the bridge and sensor devices described hereinabove. Code image update parameters and methods, as may be reviewed and managed by a management platform 700 operating in code image update mode, may include, without limitation, code image update targets, code image update contents, such as program code, custom graphics, and updated operating system instructions, other, like, features, and any combination thereof.

Where a configuration management user interface 700 operates in restart and factory reset mode, the management user interface 700 may be configured to provide for review and adjustment of restart and reset parameters and methods. Restart and reset parameters and methods may include, as examples and without limitation, warm boot settings, regarding a boot process whereby a device operating system may be re-initialized and re-started, along with any general, volatile restart parameters, cold boot settings, regarding full-power restarts, code-exchange reboots, regarding reboots wherein a bridge device restarts using application code received from a command and control server, such as the CCS, 110, of FIG. 1, above, factory reset settings, regarding an operation for resetting operating parameters to default values, other, like, settings, and any combination thereof. Further, where a configuration management platform 700 operates in restart and factory reset mode, each restart and reset sub-mode may include a valid time window in which a respective operation must complete. Further, commands configured via a configuration management platform 700 operating in restart and factory reset mode may be queued, logged, and negatively or positively acknowledged.

Where a configuration management platform 700 operates in data upload server assignment mode, the management platform 700 may be configured to provide for review and adjustment of data upload server (DUS) assignment parameters including, without limitation, DUS names, uniform resource locators (URLs), and the like, as well as any combination thereof. Where a configuration management platform 700 operates in market and environmental data mode, the management platform 700 may be configured to provide for review and adjustment of market and environmental data parameters. Market and environmental data parameters may include, as examples and without limitation, market conditions, such as grid loading, grid emergency conditions, grid events in progress, and energy pricing demand and voltage or frequency control parameters, and the like, environmental conditions, such as weather, building-specific conditions, such as building energy demand and consumption, building occupancy, building emergency conditions, other, like, market and environmental data parameters, and any combination thereof.

Where a configuration management user interface 700 operates in register update mode, the management user interface 700 may be configured to provide for review and adjustment of register update parameters. Register update parameters may include, as examples and without limitation, register names, register values, register blocks, register location specifications describing the positions of registers within one or more register blocks, and the like, as well as any combination thereof. Further, where a management user interface 700 operates in register update mode, each register or device update command configured therewith may include a time window, within which the specified operation must complete. Further, register update commands configured via a management platform 700 operating in register update mode may be queued, logged, and negatively or positively acknowledged.

Figure 7B:
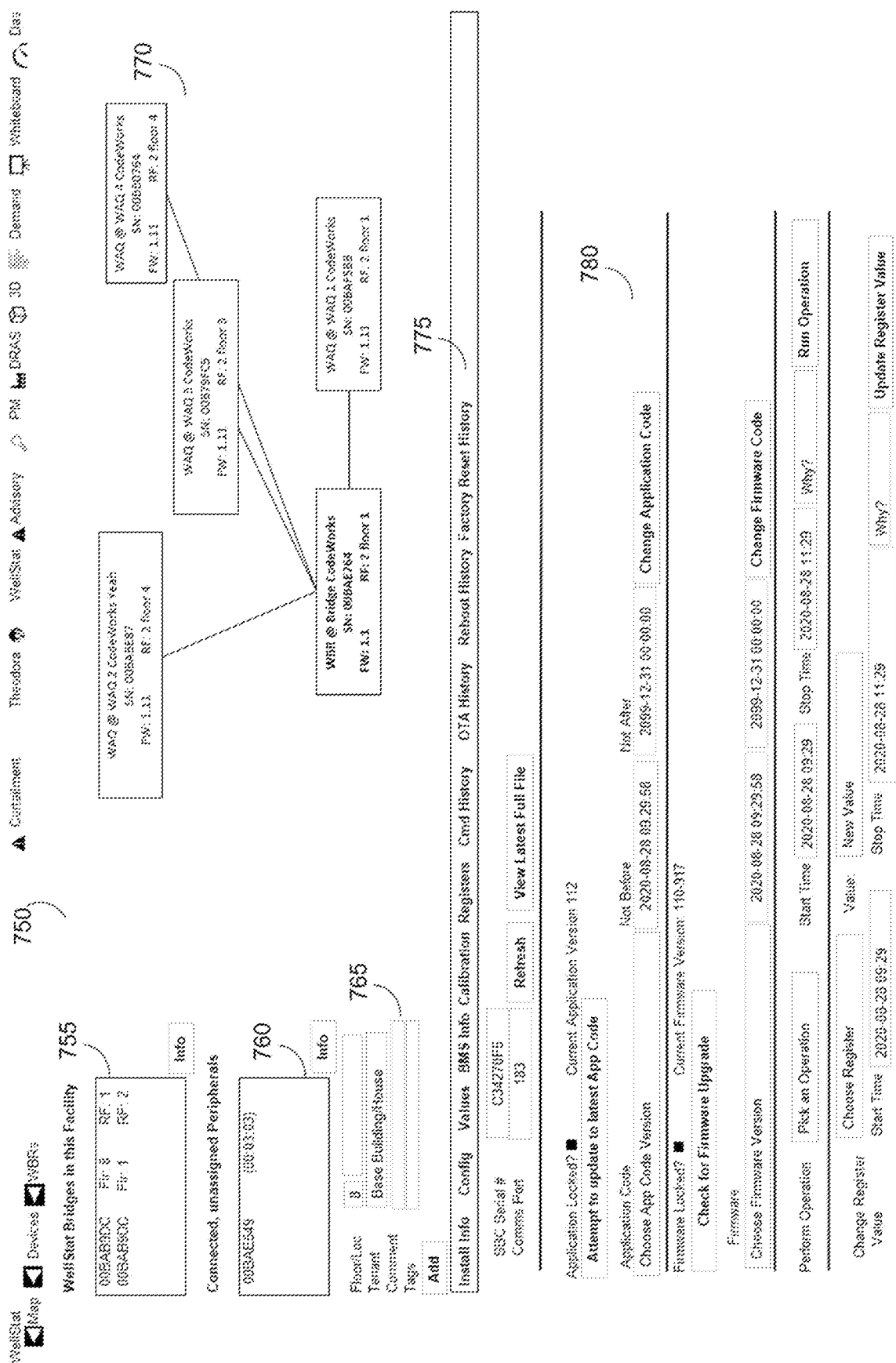
FIG. 7b is an illustration depicting a generalized user experience management interface, according to an embodiment.

FIG. 7b is an illustration depicting a generalized user experience management interface 750, according to an embodiment. A generalized user experience management interface 750 may be applicable to the management, control, and review of various network components, including, as examples, and without limitation, the bridge devices, 130, and sensors, 140, of FIG. 1, above. A generalized user experience management interface 750 may be accessible through one or more user devices connected to a cloud computing platform, such as the cloud computing platform, 120, of FIG. 1, above. User devices may include, as examples and without limitation, personal computers, smart phones, tablet computers, dedicated kiosks, and the like, as well as any combination thereof. A generalized user experience management interface 750 may be configured to include a bridge device selector 755, a sensor selector 760, a data entry tool 765, a network or architecture map 770, a management interface mode selector 775, and one or more management interface mode-specific tools 780.

A bridge device selector, 755, as may be included in a generalized user experience management interface 750, may be configured to provide for user selection of one or more bridge devices, for purposes including, without limitation, control, update, review, and the like, of bridge device parameters, settings, collected data, and the like, as well as any combination thereof. Similarly, the sensor selector 760 may be configured to provide for user selection of one or more sensor devices for purposes similar or identical to those described with respect to the bridge device selector 755. In an embodiment, the sensor selector 760 may be configured to provide for user selection of one or more sensors, wherein the one or more sensors may be connected to a bridge device selected using the bridge device selector 755.

The data entry tool 765 may be configured to provide for user modification of one or more attributes of bridge devices selected using the bridge device selector 755, of sensors selected using the sensor selector 760, as well as other, like, devices, and any combination thereof. The data entry tool 765 may be configured to provide for user modification of device attributes including, as examples and without limitation, device install locations, device comments, device tags, other, like, attributes, and any combination thereof.

The network or architecture map 770 may be configured to provide a visual representation of the configurations and interconnectivities of various bridge devices, sensor devices, and the like. The network or architecture map 770 may be configured to provide for representation of one or more devices and various attributes or features thereof. Device attributes or features which may be represented in a network or architecture map may include, as examples and without limitation, device names, device serial numbers, device firmware information, device locations, other, like, information, and any combination thereof. In an embodiment, the network or architecture map 770 may be configured to provide a visual representation of the configurations and interconnectivities of various bridge and sensor devices selected using the bridge device selector 755, the sensor selector 760, and the like, as well as any combination thereof.

The management interface mode selector 775 may be configured to provide for user selection of one or more modes of operation for the generalized user experience management interface 750, where a mode of operation includes mode-specific tools for review, management, and the like of various devices, including, without limitation, those bridge devices and sensors selected using the bridge device selector 755 and the sensor selector 760. The management interface mode selector 775 may be configured to provide for user selection of one or more modes of operation including, as examples and without limitation, device values mode, device installation information mode, device configuration management mode, building management system (BMS) mode, other, like, modes, and any combination thereof. Further, where a management interface mode is selected using the management interface mode selector 775, the general user experience management interface 750 may be configured to include one or more management interface mode-specific tools 780, where the provided mode-specific tools may be configured to provide for user review and management of device attributes, features, data, and the like, related to the selected management interface mode. In the example general user experience management interface 750 depicted in the illustration, a device configuration mode is selected, and relevant management interface mode-specific tools 780 are included in the general user experience management interface 750, including device communication parameter tools, device firmware management tools, device operations management tools, device register management tools, and configuration management history tools. It may be understood that, while the described tools are included in the illustration depicted in the interface, other, like, tools and modes may be equally applicable without loss of generality or departure from the scope of the disclosure.

Figure 8:
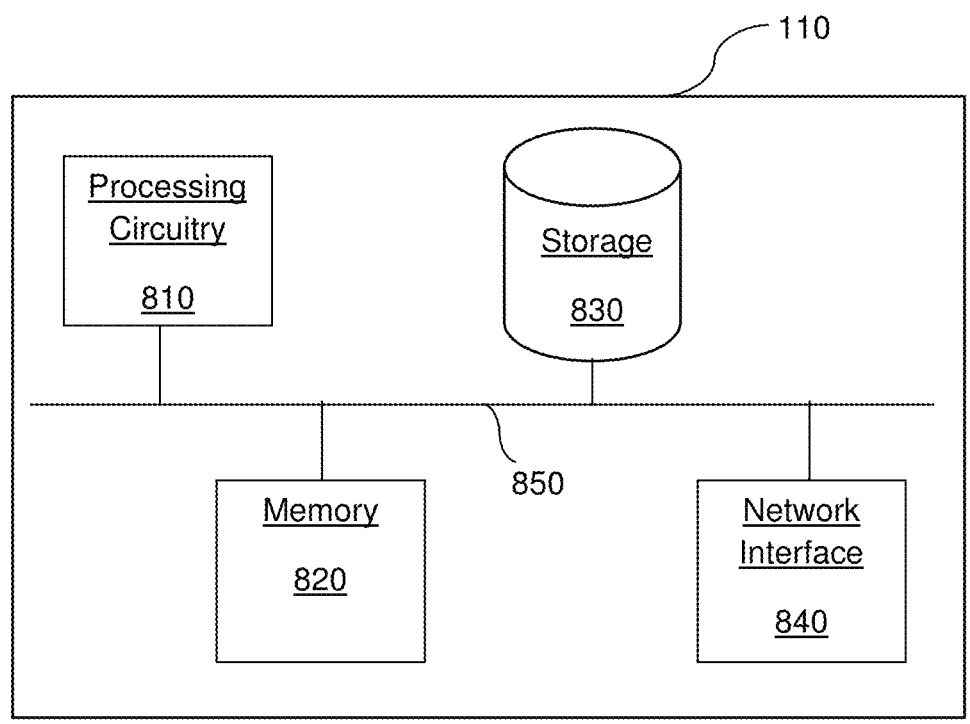
FIG. 8 is an example schematic diagram of a command and control server, according to an embodiment.

FIG. 8 is an example schematic diagram of the CCS 110, according to an embodiment. The command and control server 110 includes a processing circuitry 810 coupled to a memory 820, a storage 830, and a network interface 840. In an embodiment, the components of the CCS 110, may be communicatively connected via a bus 850.

The processing circuitry 810 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 820 may be volatile (e.g., random access memory, etc.), non-volatile (e.g., read only memory, flash memory, etc.), or a combination thereof.

In one configuration, software for implementing one or more embodiments disclosed herein may be stored in the storage 830. In another configuration, the memory 820 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 810, cause the processing circuitry 810 to perform the various processes described herein.

The storage 830 may be magnetic storage, optical storage, and the like, and may be realized, for example, as flash memory or another memory technology, compact disk-read only memory (CD-ROM), Digital Versatile Disks (DVDs), or any other medium which can be used to store the desired information.

The network interface 840 allows the CCS 110 to communicate with the various components, devices, and systems described herein for assuring building air quality.

It should be understood that the embodiments described herein are not limited to the specific architecture illustrated in FIG. 8, and other architectures may be equally used without departing from the scope of the disclosed embodiments.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A method for centrally assuring building air quality, comprising:
    collecting, from a set of sensors of a plurality of sensors, at least indoor air quality data, wherein the plurality of sensors are installed in different locations within a building;
    analyzing the collected indoor air quality data to determine an air-quality level across different locations within the building;
    triggering a determination as to whether an adjustment to at least one control device is required, wherein the determination is triggered and performed based only on the determined indoor air-quality level and at least one energy-consumption parameter, the determining further comprises comparing the at least one energy-consumption parameter to an energy consumption parameter rule in effect for the building from amongst a plurality of available energy consumption parameter rules and wherein values of the energy-consumption before the adjustment and after the adjustment, if performed, are employed in the determining, and wherein the energy consumption rule ensures that an associated with changes to the energy consumption does not exceed a prescribed value; and
    actuating at least one building control device when an adjustment is required, wherein actuating at least one building control device allows for control of air quality across different locations within the building.

2. The method of claim 1, wherein a sensor of the plurality of sensors is any one of: a temperature sensor, a pressure sensor, a humidity sensor, a particulate concentration level sensor, an Ozone sensor, a light senor, a gas sensor, a TVOC sensor, a carbon dioxide ($CO_2$) sensor, a barometric pressure sensor, and a differential pressure sensor.

3. The method of claim 1, wherein determining at least an adjustment further comprises:
    comparing the determined indoor air-quality level to an air-quality level rule set for the building; and
    determining that the adjustment is required when the air-quality level rule and the energy-consumption parameter rule are satisfied.

4. The method of claim 3, wherein each of the at least one air-quality level rule and the at least one energy-consumption parameter rule is an adjustable rule.

5. The method of claim 1, wherein an energy-consumption rule defines at least one of: a maximum allowed energy consumption and a cost for consumed energy, wherein the energy-consumption rule is set with different values for different hours of a day.

6. The method of claim 3, further comprising:
    generating a building demand response based on at least an energy usage trend parameter and the energy-consumption rule; and
    optimizing the actuation of the at least one building control device based on the building demand response.

7. The method of claim 1, wherein each of the at least one building control devices includes any one of: a device for regulating temperature, a device for regulating humidity, and a device for regulating airflow.

8. The method of claim 1, wherein one or more of the plurality of sensors are connected to a bridge device, wherein the bridge device allows connectivity to a server which centrally controls the sensors and the at least one building control device.

9. The method of claim 1, wherein the actuation of the at least one building control device is performed via a building management system.

10. The method of claim 8, further comprising:
receiving an update request from at least one bridge device;
processing the bridge update request;
collecting, in response to the bridge update request, at least configuration data; and
pushing configuration data to at least the bridge device from which the request is received.

11. The method of claim 10, wherein the configuration data includes any one of: program code, custom graphics, and updated operating system programming instructions.

12. The method of claim 10, further comprising:
collecting data features from a bridge device, wherein a data feature relates to operation of the bridge device or a sensor connected thereto;
processing the collected data features; and
displaying one or more processed and unprocessed data features through a user interface (UI).

13. The method of claim 1, further comprising:
actuating at least one building control device to improve wellness of occupants in the building, wherein the actuation for improving wellness is based at least on sensor readings related to air filter status and air quality contamination.

14. The method of claim 1, wherein the method is performed by a command and control server, wherein the command and control server is deployed in a cloud computing platform.

15. The method of claim 1, further comprising:
receiving data feeds from at least one cloud service; and
determining whether an adjustment to at least one building control device is required based on the data feeds.

16. A non-transitory computer readable medium having stored thereon instructions for causing a processing circuitry to execute a process for centrally assuring building air quality, the process comprising:
collecting, from a set of sensors of a plurality of sensors, at least indoor air quality data, wherein the plurality of sensors are installed in different locations within a building;
analyzing the collected indoor air quality data to determine an air-quality level across different locations within the building;
triggering a determination as to whether an adjustment to at least one control device is required, wherein the determination is triggered and performed based only on the determined indoor air-quality level and at least one energy-consumption parameter, the determining further comprises comparing the at least one energy-consumption parameter to an energy consumption parameter rule in effect for the building from amongst a plurality of available energy consumption parameter rules and wherein values of the energy-consumption before the adjustment and after the adjustment, if performed, are employed in the determining, and wherein the energy consumption rule ensures that an associated with changes to the energy consumption does not exceed a prescribed value; and
actuating at least one building control device when an adjustment is required, wherein actuating at least one building control device allows for control of air quality across different locations within the building.

17. A system for centrally assuring building air quality, comprising:
a processing circuitry; and
a memory, the memory containing instructions that, when executed by the processing circuitry, configure the system to:
collect, from a set of sensors of a plurality of sensors, at least indoor air quality data, wherein the plurality of sensors are installed in different locations within a building;
analyze the collected indoor air quality data to determine an air-quality level across different locations within the building;
trigger a determination as to whether an adjustment to at least one control device is required, wherein the determination is triggered and performed based only on the determined indoor air-quality level and at least one energy-consumption parameter, the determining further comprises comparing the least at one energy-consumption parameter to an energy consumption parameter rule in effect for the building from amongst a plurality of available energy consumption parameter rules and wherein values of the energy-consumption before the adjustment and after the adjustment, if performed, are employed in the determining, and wherein the energy consumption rule ensures that an associated with changes to the energy consumption does not exceed a prescribed value; and
actuate at least one building control device when an adjustment is required, wherein actuating at least one building control device allows for control of air quality across different locations within the building.

18. The system of claim 17, wherein a sensor of the plurality of sensors is any one of: a temperature sensor, a pressure sensor, a humidity sensor, a particulate concentration level sensor, an Ozone sensor, a light senor, a gas sensor, a TVOC sensor, a carbon dioxide ($CO_2$) sensor, a barometric pressure sensor, and a differential pressure sensor.

19. The system of claim 17, wherein the system is further configured to:
compare the determined indoor air-quality level to an air-quality level rule set for the building; and
determine that the adjustment is required when the air-quality level rule and the energy-consumption parameter rule are satisfied.

20. The system of claim 17, wherein each of the at least one air-quality level rule and the at least one energy-consumption rule is an adjustable rule.

21. The system of claim 17, wherein an energy-consumption rule defines at least one of: a maximum allowed energy consumption and a cost for consumed energy, wherein an energy-consumption rule is set with different values for different hours of a day.

22. The system of claim 19, wherein the system is further configured to:
generate a building demand response based on at least an energy usage trend parameter and the energy-consumption rule; and optimize the actuation of the at least one building control device based on the building demand response.

23. The system of claim 17, wherein each of the at least one building control devices includes any one of: a device for regulating temperature, a device for regulating humidity, and a device for regulating airflow.

24. The system of claim 17, wherein one or more of the plurality of sensors are connected to a bridge device, wherein the bridge device allows connectivity to a server which centrally controls the sensors and the at least one building control device.

25. The system of claim 17, wherein the actuation of the at least one building control device is performed via a building management system.

26. The system of claim 24, wherein the system is further configured to:
receive an update request from at least one bridge device;
process the bridge update request;
collect, in response to the bridge update request, at least configuration data; and
push configuration data to at least the bridge device from which the request is received.

27. The system of claim 26, wherein the configuration data includes any one of: program code, custom graphics, and updated operating system programming instructions.

28. The system of claim 26, wherein the system is further configured to:
collect data features from a bridge device, wherein a data feature relates to operation of the bridge device or a sensor connected thereto;
process the collected data features; and
display one or more processed and unprocessed data features through a user interface (UI).

29. The system of claim 17, wherein the system is further configured to:
actuate at least one building control device to improve wellness of occupants in the building, wherein the actuation for improving wellness is based at least on sensor readings related to air filter status and air quality contamination.

30. The system of claim 17, wherein the system is deployed in a cloud computing platform.

31. The system of claim 17, wherein the system is further configured to:
receive data feeds from at least one cloud service; and
determine whether an adjustment to at least one building control device is required based on the data feeds.

* * * * *